United States Patent
Bjarnason et al.

(10) Patent No.: US 8,597,368 B2
(45) Date of Patent: *Dec. 3, 2013

(54) PROSTHETIC LINER WITH CONTINUOUS DISTAL END AREA

(75) Inventors: Asmundur Bergmann Bjarnason, Reykjavik (IS); Sigurdur Asgeirsson, Gardabaer (IS)

(73) Assignee: Ossur HF, Reykjavik (IS)

(*) Notice: Subject to any disclaimer, the term of this patent is extended or adjusted under 35 U.S.C. 154(b) by 0 days.

This patent is subject to a terminal disclaimer.

(21) Appl. No.: 13/397,893

(22) Filed: Feb. 16, 2012

(65) Prior Publication Data

US 2012/0150320 A1 Jun. 14, 2012

Related U.S. Application Data

(63) Continuation of application No. 12/731,513, filed on Mar. 25, 2010, now Pat. No. 8,123,818.

(60) Provisional application No. 61/163,952, filed on Mar. 27, 2009.

(51) Int. Cl.
*A61F 2/80* (2006.01)

(52) U.S. Cl.
USPC .......................................................... 623/36

(58) Field of Classification Search
USPC ................. 623/32–37; 2/274–275; 36/21, 57; 442/248; 112/418, 426; 604/385.01, 604/385.03
See application file for complete search history.

(56) References Cited

U.S. PATENT DOCUMENTS

| | | | |
|---|---|---|---|
| 2,325,656 A | 8/1943 | Brophy | |
| 4,319,413 A | 3/1982 | Mattil | |
| 4,474,573 A | 10/1984 | Detty | |
| 4,554,749 A * | 11/1985 | Ostrander | 36/102 |
| 4,885,828 A | 12/1989 | Kozlowski | |
| 5,244,716 A | 9/1993 | Thornton et al. | |
| 5,830,237 A | 11/1998 | Kania | |
| 5,885,674 A | 3/1999 | Maemoto et al. | |
| 6,076,284 A | 6/2000 | Terlizzi | |
| 6,136,039 A | 10/2000 | Kristinsson et al. | |
| 6,171,431 B1 | 1/2001 | Gallagher, Jr. et al. | |
| 6,406,499 B1 | 6/2002 | Kania | |
| 6,485,776 B2 | 11/2002 | Janusson et al. | |
| 6,626,952 B2 | 9/2003 | Janusson et al. | |

(Continued)

FOREIGN PATENT DOCUMENTS

WO 01/67842 A1 9/2001

OTHER PUBLICATIONS

Iceross® Confort® Locking/Cushion product information brochure, Mar. 27, 2009, 3 pages.

(Continued)

*Primary Examiner* — David Isabella
*Assistant Examiner* — Marcia Hoffman
(74) *Attorney, Agent, or Firm* — Workman Nydegger (57) ABSTRACT

A tubular liner has an open proximal end and a closed-end distal area, and a fabric layer continuously defining an exterior surface of the liner without interruption. A polymeric layer having first and second surfaces is bonded to an interior surface of the fabric layer. A seam is formed by opposed sides of the fabric layer joined together and forming an excess portion directed toward the cavity of the liner. The excess portion is embedded in the polymeric layer.

15 Claims, 5 Drawing Sheets

(56) References Cited

U.S. PATENT DOCUMENTS

| | | |
|---|---|---|
| 6,706,364 B2 | 3/2004 | Janusson et al. |
| 6,852,269 B2 | 2/2005 | Eberle et al. |
| 6,964,688 B1 | 11/2005 | Kania |
| 7,001,563 B2 | 2/2006 | Janusson et al. |
| 7,025,793 B2 | 4/2006 | Egilsson |
| 7,118,602 B2 | 10/2006 | Bjarnason |
| 7,169,189 B2 | 1/2007 | Bjarnason et al. |
| 7,291,182 B1 | 11/2007 | Kania |
| 7,351,264 B2 | 4/2008 | Wilson |
| 8,123,818 B2 * | 2/2012 | Bjarnason et al. .............. 623/36 |
| 2002/0165619 A1 | 11/2002 | Hellberg |
| 2002/0183859 A1 | 12/2002 | Houser |
| 2003/0181989 A1 | 9/2003 | Eberle et al. |
| 2005/0115112 A1 * | 6/2005 | Bonfanti ........................... 36/97 |
| 2005/0155137 A1 * | 7/2005 | Berger ............................. 2/239 |
| 2005/0240283 A1 | 10/2005 | Kania |
| 2006/0165939 A1 * | 7/2006 | Hottner .......................... 428/57 |
| 2007/0027556 A1 | 2/2007 | Wilson |
| 2007/0043450 A1 | 2/2007 | Pickering et al. |
| 2007/0061017 A1 | 3/2007 | Wilson |
| 2007/0123998 A1 | 5/2007 | Egilsson et al. |
| 2008/0188949 A1 | 8/2008 | MacKenzie |
| 2008/0221705 A1 | 9/2008 | Scussel |
| 2008/0221706 A1 | 9/2008 | Scussel et al. |

OTHER PUBLICATIONS

Iceross® Dermo, product information sheets from Internet, http://www.ossur.com/prosthetics/liners/dermo, Mar. 27, 2009, 2 sheets.

Military inStep: Prosthetic Socks and Liners, product information sheets from Internet, http//www.amputee-coalition.org/military-in-step/prosthetic-socks, Mar. 27, 2009, 3 pages.

Prosthetic & Orthotic Update NewsLetter, No. 32, Internet Search conducted Mar. 27, 2009, 4 pages.

Walopur® Platilon@U, Product Information Brochure of Epurex Films GmbH & Co., KG, Internet Search result conducted Mar. 27, 2009, 2 pages.

International Search Report issued in related PCT/US2010/000925, dated Jun. 2, 2010.

* cited by examiner

PROSTHETIC LINER WITH CONTINUOUS DISTAL END AREA

CROSS-REFERENCE TO RELATED APPLICATION

This application is a continuation of U.S. patent application Ser. No. 12/731,513, filed on Mar. 25, 2010, issued as U.S. Pat. No. 8,123,818 on Feb. 28, 2012, which claims the benefit of priority of the filing date of U.S. provisional application no. 61/163952, filed on Mar. 27, 2009, both of which are incorporated by reference herein in their entirety.

FIELD OF THE INVENTION

This invention relates to a prosthetic liner adapted to envelop a residual limb. Specifically, the prosthetic liner has a seam defined along sections of at least one fabric layer such that the exterior and interior surfaces of the liner generally define continuous surfaces without interruption.

BACKGROUND

Prosthetic liners are well known in the art of the prosthetic devices. It is highly desirable that these liners conform closely to the residual limb, accommodate surface contours and sub-surface bone elements of the residual limb, and provide a comfortable cushion between the residual limb and a hard socket of a prosthesis that is to be fitted over the residual limb.

Special polymeric rubber or elastomer materials, such as silicone compositions, have been formulated as suitable substances for prosthetic liners. These elastomer materials having an appropriate hardness (or softness), elongation, tensile, and other properties, such as bio-inertness (resulting in no skin reaction), have been successfully used for prosthetic liners.

A prosthetic liner which does not lock to a hard socket is generally referred to as a "cushion" liner. Cushion liners are designed to accommodate residual limbs with fragile and exposed tissues, bony prominences prone to pressure peaks, and conical residual limbs. These cushion liners can be geometrically configured to greatly decrease the need for custom-made prosthetic liners. The distal end of these liners often includes a distal end cap embedded into the liner.

A distal end cap may include components made from aluminum or other metal, or rigid plastics such as Nylon. The end cap can create discomfort to the user since it interferes in allowing the liner to conform to the geometry of the limb, and impede pressure distribution of the liner over the residual limb. The end cap may also limit stretchability of the liner.

While effective solutions have been proposed and implemented, it is desirable to improve the comfortibility of such liners or sleeves to increase their ability to conform to irregularities on a residual limb, and accommodate a wider variety of limbs with fewer sizes of liners, while maintaining sufficient strength and durability. Moreover, it is particularly desirable to provide a liner or sleeve arranged to distribute pressure of the liner against a prosthesis while providing superior stretchability over known liners and sleeves.

For the foregoing reasons, there is a need to provide improved liners and sleeves that impart improved conformability, pressure distribution, and stretchability while maintaining sufficient durability and strength for their requisite applications.

SUMMARY

In accordance with a first embodiment of the invention, a tubular prosthetic liner is adapted to envelop a residual limb. The liner has an open proximal end arranged to permit entry of the residual limb into a cavity of the liner defined by a continuous inner surface and a closed-end distal end area arranged to receive the residual limb such that the residual limb is closely enveloped by the liner. The liner defines an exterior surface generally conforming to the residual limb.

The liner includes an elasticized fabric layer defining outer and inner surfaces. In this embodiment, a seam is formed across the distal end area of the liner and closes the distal end area of the fabric layer. The first fabric layer surface continuously defines the exterior surface of the liner, via the seam, at the distal end area of the liner without interruption, such as by substantial recesses or protruding features.

According to this embodiment, the liner includes a first polymeric layer having inner and outer surfaces. The outer layer surface is intimately and continuously bonded to the inner surface of the fabric layer. The liner also includes a second polymeric layer having inner and outer surfaces. The outer surface of the second polymeric layer surface is contiguous and integrally secured to the inner surface of the first polymeric layer. The second polymeric layer is substantially thicker than the first polymeric layer. The inner surface of the second polymeric layer defines the interior surface of the liner which is continuously smooth.

In a variation of this liner embodiment, the liner only includes a single polymeric layer such that one of the first and second polymeric layers described above may be eliminated. In yet other variation, the liner is not limited to a single or two polymeric layers.

The seam is preferably formed by opposed edge portions of the fabric layer joined by a welding element. The welding element may be a polymeric film which is contiguously and integrally joined to the opposed sides of the fabric layer. The seam may form an excess portion directed toward the interior cavity of the liner but this excess portion is buried or embedded by the second polymeric layer.

The liner distal end area may have an arcuate outer wall defining radii of curvature centered along a liner longitudinal axis of external symmetry, with the seam tracing at least along the radii of curvature. The seam may correspond exactly to the curvature of the liner distal end area.

In a variation of the seam, the seam is defined by a stitched seam of the opposed edge portions of the fabric layer. The stitched seam only minimally protrudes from the exterior surface of the liner, thereby avoiding any substantially raised surfaces which could impede the usage of the liner in connection with a socket.

According to this embodiment, the fabric layer is an elasticized fabric layer. The distal end area of the fabric layer is preferably arranged in a permanent distended condition such that the distal end area of the fabric layer has a continuous, surface without interruption.

The first polymeric layer may have a thickness that is substantially less than a thickness pertaining to the second polymeric layer. Moreover, the second polymeric layer may have a variable thickness increasing from the proximal end to the distal end area. The distal end area thickness of the second polymeric layer may be generally uniform.

The first and second polymeric layers may include a silicone elastomer. The first and second polymeric layers may also each have different hardnesses relative to one another; the second polymeric layer having a lower hardness than the hardness of the first polymeric layer.

The second polymeric layer may comprise a composite including silicone elastomer and silicone oil dispersed through the silicone elastomer. Also, the second polymeric layer may contain a plurality of hollow microspheres dispersed through the polymeric material.

The liner may include a distension controlling reinforcement matrix embedded in the second polymeric layer over the distal end area of the liner. The reinforcement matrix contains reinforcement elements that provide substantial stiffness against elongation of the liner in a direction along the liner length. These reinforcement elements preferably do not provide substantial resistance against distension of the second polymeric layer in directions transverse to the liner length.

The reinforcement matrix is arranged so as not to interfere with the opposed sides of the fabric layer. According to one embodiment, the opposed sides of the fabric layer extend below in the polymeric layer below the reinforcement matrix.

In variations of the embodiment, the liner may be provided without a reinforcement matrix.

Embodiments of the invention are not limited to a seam located at a distal end area of the liner. Instead, multiple fabric sections may be combined to form the fabric layer. These fabric sections are preferably joined in a similar manner to the aforementioned seam, either by welding or stitching.

An exemplary embodiment includes a second fabric section secured to a first fabric section. The second fabric section is surrounded in its entirety by the first fabric section. The second fabric section may have greater stiffness properties to accommodate certain anatomy of the residual limb, such as a knee. The second fabric section may be arranged in a variety of different shapes according to the different anatomy it is to correspond to, and it may likewise be oriented according to desired results from the multiple section fabric layer. Moreover, the fabric layer may include a plurality of different fabric sections, preferably each connected to one another according to the aforementioned seams.

In another exemplary embodiment, first and second fabric sections are secured to each other along a longitudinal seam. The first fabric section may correspond to the anterior portion of the residual limb and the second fabric section may correspond to the posterior portion of the residual limb.

In yet another exemplary embodiment, first and second circumferential fabric sections are secured together along a circumferential seam. The first fabric section may correspond to the distal end area of the liner so as to envelop the distal end area of the residual limb. The second fabric section is arranged to at least envelop portions of the residual limb above or directed more towards a proximal end of the liner.

In each of these embodiments, the first and second fabric sections may have different properties, for example stiffness, surface texture, thickness, hardness.

According to a variation of the embodiments described herein, an umbrella connector may be embedded into a liner having a seam. The umbrella connector is generally adjacent to the interior surface of the fabric layer. The umbrella connector includes a connecting end that extends through an opening defined across a distal end area of the liner and over the seam effectively removing part of the seam. A distal end cap may be formed or bonded along the exterior surface of the distal end area of the liner, and surrounding a portion of the connecting end.

The liner may be formed with or without the distal end cap, and a reinforcement matrix may be used in combination with the umbrella connector.

The embodiments described herein have superior cushioning and conform to the distal end of residual limb so as to contribute to more equal pressure distribution. This significant benefit, as will become apparent below, will be understood by the provision of a distal end area seam that eliminates the need for any distal end cap found in conventional comfort liners.

The numerous advantages, features and functions of the various embodiments of the sleeve or liner with a continuous distal end area will become readily apparent and better understood in view of the following description and accompanying drawings. The following description is not intended to limit the scope of the sleeve or liner, but instead merely provides exemplary embodiments for ease of understanding.

In the various figures, similar elements are provided with similar reference numbers. It should be noted that the drawing figures are not necessarily drawn to scale, or proportion, but instead are drawn to provide a better understanding of the components thereof, and are not intended to be limiting in scope, but rather provide exemplary illustrations.

DETAILED DESCRIPTION OF VARIOUS EMBODIMENTS

The embodiments described herein may be adapted as a prosthetic liner, for example a cushion liner, which forms an interface between the skin of a residual limb and preferably rigid or semi-rigid socket. The prosthetic liner stabilizes soft tissues, minimizes pistoning (stretching), helps to improve circulation, and adds comfort.

An example of a method for making a socket, as is readily understood by the skilled artisan in the field of prosthetics, is described in U.S. Pat. No. 7,438,843, granted Oct. 21, 2008, the entirety of which is incorporated herein by reference.

Figure 1:
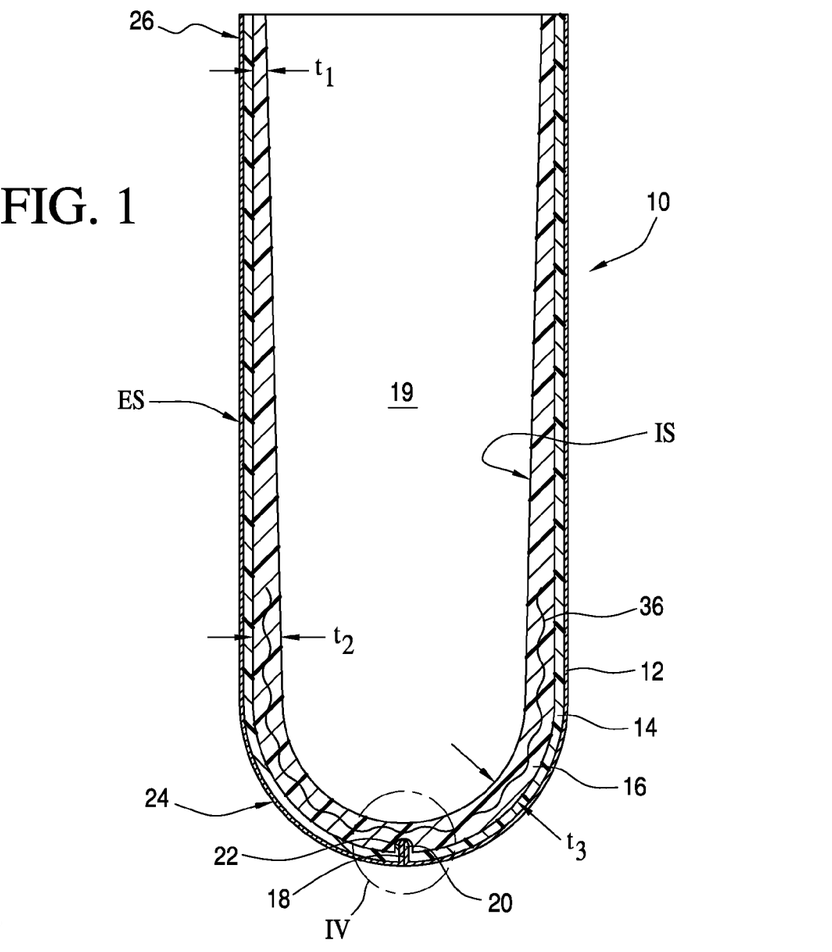
FIG. 1 is a cross-sectional view showing a first embodiment of the liner according to the invention.

In an embodiment of the liner, FIG. 1 schematically illustrates in a cross-section view a prosthetic liner 10 arranged as a tubular liner adapted to envelop a residual limb. The liner has an open proximal end arranged to permit entry of the residual limb into an interior cavity 19 formed by the liner. The cavity is defined by a continuous interior surface IS and a closed-end distal end area such that the cavity is arranged to receive and closely envelop residual limb. The liner defines an exterior surface ES which generally conforms to the residual limb.

The liner 10 is formed in part by an elasticized fabric layer 12 along its exterior surface ES, an intermediate, first polymeric layer 14, and a second polymeric layer 16 formed along the interior surface IS. A seam 18 is formed across the distal end area 24 of the liner and closes opposed edge portions 20, 22 of the fabric layer 12 at the distal end area 24 The entire assembly of the fabric layer, the first polymeric layer, and the second polymeric layer is at least freely radially elastically distendable.

The fabric layer 12 defines outer and inner surfaces whereby the outer surface continuously forms the exterior surface ES of the liner 10. The first polymeric layer 14 has inner and outer surfaces, and the outer surface is intimately and continuously bonded to the inner surfaces of the fabric layer 12. The second polymeric layer 16 has inner and outer surfaces wherein the outer surface of the second polymeric layer 16 is contiguous and integrally secured to the inner surface of the first polymeric layer 14.

The second polymeric layer 16 is substantially thicker than the first polymeric layer as evidenced by the thicknesses $t_1$, $t_2$ and $t_3$. In particular, the thickness of the second polymeric layer 16 is substantially uniform at the distal end area 24 of the liner, and progressively tapers towards the proximal end area 26.

Figure 4:
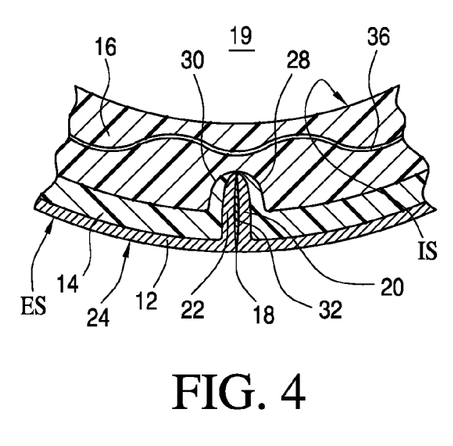
FIG. 4 is an enlarged sectional view taken from FIG. 1.

The inner surface of the second polymeric layer 16 defines the inner surface IS of the liner 10. The inner surface of the second polymeric layer 16 is continuously smooth meaning that it is without interruption and does not form any substantial recesses or protrusions, as shown in FIGS. 1 and 4. The smooth surface allows for pressure relief and comfortably accommodates bony prominences, sensitive areas and scarred tissue of the residual limb.

The opposed edge portions 20, 22 are effectively embedded or buried within the thickness $t_3$ of the second polymeric layer 16. The thickness $t_3$ and extent of the excess of the opposed edge portions is arranged so that the wearer does not feel the excess of the opposed edge portions 20, 22 when the liner is worn on the residual limb.

The fabric layer is normally air permeable and may be formed from a flat knit elasticized fabric. The inner surface of the fabric layer is coated with the first polymeric layer 14 defined as a thin layer of cured silicone elastomer preferably partially embedded in the fibers of the textile without completely penetrating the textile. The fabric layer is preferably seamless along the sides of the liner with the exception of the seam located at the distal end area.

The second polymeric layer is preferably a silicone elastomer that has hardness properties lower than hardness properties of the first polymeric layer. Moreover, the second polymeric layer preferably has a thickness greater than a thickness of the first polymeric layer. The second polymeric layer may include hollow thermoplastic microspheres, silicone oil, and/or one or more skin treatment agents. Such skin treatment agents may include petroleum jelly and aloe vera.

The fabric layer, and the first and second polymeric layers may be formed in accordance with any of the following U.S. Pat. Nos. 6,136,039, 6,626,952, 6,485,776, 6,706,364, 7,001, 563 and 7,118,602, each of which are incorporated herein by reference in their entirety. The liner embodiments of the pending application may be configured to include any of the features of the aforementioned patents As depicted in FIGS. 1 and 4, an embodiment of the liner 10 may include a distension controlling reinforcement matrix 36 embedded in the second polymeric layer 16 over the distal end area 24 of the liner. The reinforcement matrix 36 contains reinforcement elements that provide substantial stiffness against elongation of the liner in a direction along the liner length and do not provide substantial resistance against distension of the second polymeric layer in directions transverse to the liner length. The reinforcement elements may comprise interlocked fibers such as a circular knit tubular fabric that strongly resist longitudinal elongation but readily distends radially. An example of a reinforcement matrix is described by U.S. Pat. No. 6,706,364.

In variations of the liner described herein, the liner may be provided without a reinforcement matrix.

It will be pointed out that the first and second polymeric layer construction may be substituted with a single polymeric layer, having either consistent material properties, or material properties akin to the dual layer construction described above. In other variations, the liner may have additional polymeric layers to the first and second polymeric layer construction.

Figure 2:
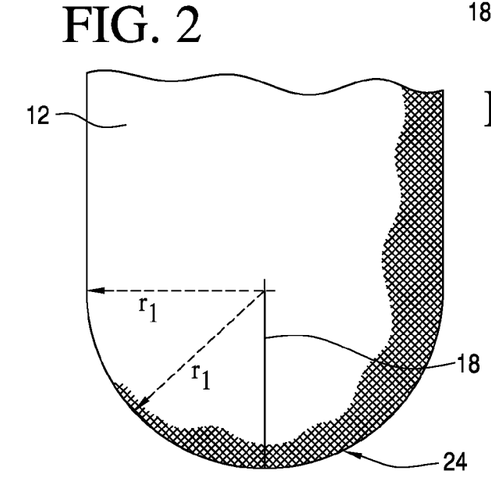
FIG. 2 is a sectional elevational view showing an outer surface of the liner according to FIG. 1.

FIG. 2 depicts the distal end area 24 as having an arcuate outer wall defining a radius $r_1$ of curvature centered along a liner longitudinal axis of external symmetry. The seam 18 preferably traces along the radii of curvature and is generally restricted in length on opposed sides by the height of the radius $r_1$. The seam 18 may be configured to extend on opposed sides of the liner 10, either above or below the height of the radius $r_1$.

Figure 3:
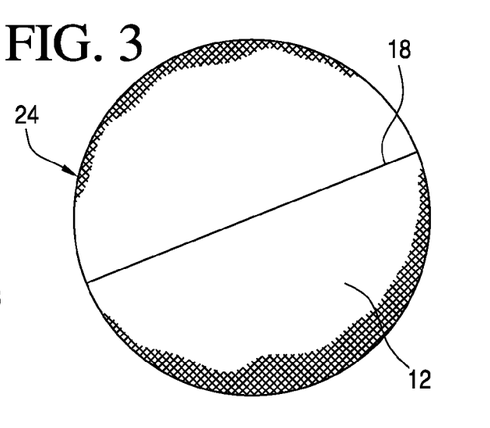
FIG. 3 is a bottom plan view showing an outer surface at a distal end area of the liner according to FIG. 1.

As shown by FIG. 3, the distal end area 24 of this liner embodiment along the exterior surface is continuous, without interruption. At least the distal end area 24 of the fabric layer 12 is arranged in a permanent distended condition thereby preferably preventing the seam from puckering or causing a recess to be formed along the distal end of the liner. Nonetheless, despite the permanent distended configuration, the fabric layer 12 is still capable of additional distension when the liner 10 is placed over a residual limb.

In observing FIG. 4, the seam 18 is welded and air-tight. The seam 18 is preferably formed by the opposed edge portions 20, 22 of the fabric layer 12 joined by a welding element 32. Also shown are edge portions 28, 30 of the first polymeric layer bonded to the opposed edge portions 20, 22. The excess of the opposed edge portions 20, 22 is directed toward the interior cavity 19 of the liner but this excess portion is embedded or buried by the second polymeric layer 16 so as to minimize or eliminate any notice by the wearer of when the liner is donned over the residual limb.

According to one variation, the opposed edge portions are entirely embedded in at least one of the polymeric layers.

It is preferred that the seam is minimized to avoid any discomfort that could arise with the buried excess portion of the seam on the interior side of the liner. The seam can be modified in accordance with a variety of different lengths depending on the geometry of the liner.

While the opposed edge portions 20, 22 are depicted as being generally upright, the opposed edge portions 20, 22 can be adapted so that they are folded or oriented askew in a manner to minimize protruding into the thickness of the second polymeric layer.

The welding element 32 may be a polymeric film which is contiguously and integrally joined to the opposed sides of the fabric layer. A preferred welding film is a polyurethane film under the trade name WALOPUR and distributed by Epurex Films GmbH. A variety of the types of films that may be used include any type of thermoformable film, whether elastic or inelastic. Also, thermoset films may be used including those having two components.

Figure 5:
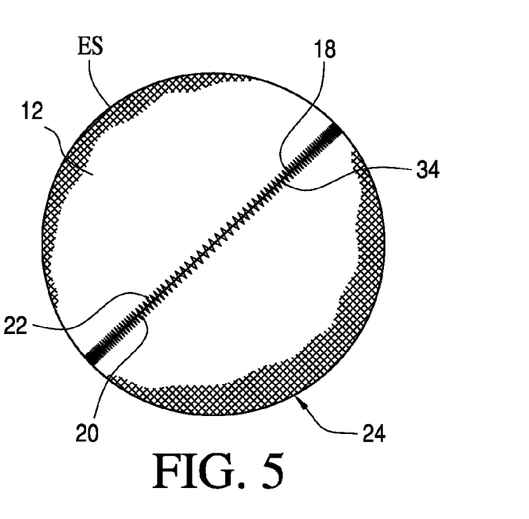
FIG. 5 is a bottom plan view showing an outer surface at a distal end area of a variation of the liner according to FIG. 1.

FIG. 5 illustrates an alternative embodiment of the seam 18 wherein the seam is formed by stitching the opposed edge portions 20, 22 of the fabric layer. The stitching 34 is exposed on the exterior surface ES of the distal end area 24. The stitching may be used in embodiments of the liner with or without the welding strip.

Figure 6:
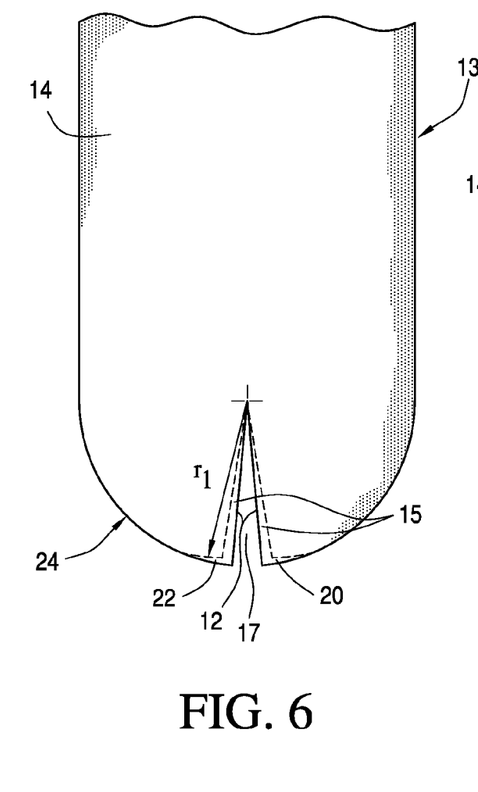
FIG. 6 is an elevational view showing an inside-out liner in a production step of the liner according to the embodiment of FIG. 1 prior to sealing the distal end area.
Figure 7:
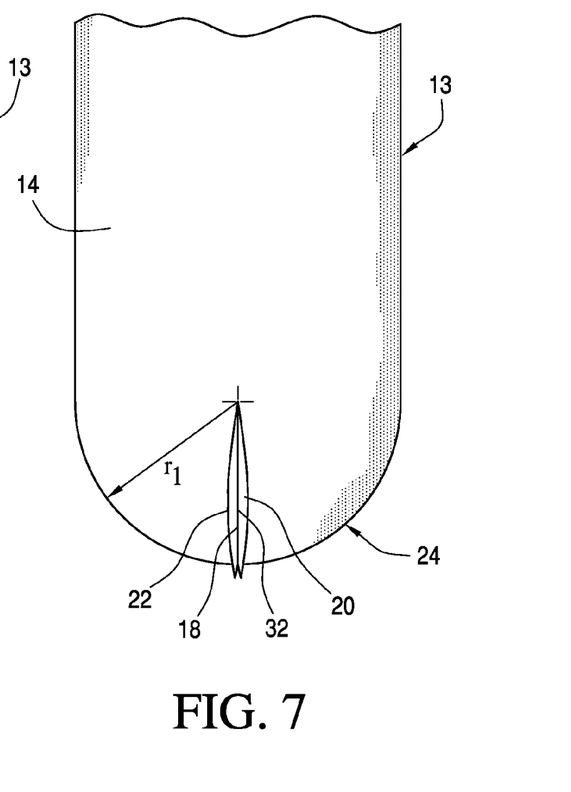
FIG. 7 is an elevational view showing an inside-out liner in a production step of the liner according to the embodiment of FIG. 1 after sealing the distal end area.

In observing FIGS. 6 and 7, production steps for forming the seam are exemplified. The liner 13 is in an early production form wherein the fabric layer 12 has been coated with the thin first polymeric layer 14. The liner 13 is depicted in an inside out configuration wherein the first polymeric layer 14 forms the exterior surface for the purpose of forming the seam.

The tubular fabric layer 12 is first cut according to a pattern of excess portion 15 accounting for the opposed edge portions 20, 22. The pattern is such that it permits the seam to be formed and the finalized liner forms the definitive shape of the liner 13 in a generally symmetrical configuration. The distal end area 24 of the liner 13 includes a slit 17 defined between the opposed edge portions 20, 22.

The welding film 32 is inserted between the opposed edge portions 20, 22. The opposed edge portions 20, 22 are brought toward one another under pressure and heat. The heat causes the film to bond the opposed edge portions 20, 22 to each other. Any excess welding film protruding from the seam and the opposed edge portions 20, 22 is trimmed from the liner 13.

Upon bonding of the opposed edge portions 20, 22, the seam 18 is formed. The excess portion 15 forms along the seam 18, such that when the liner 13 is flipped to its normal configuration, the excess portion 15 extends along the interior of the liner and is generally directed to the cavity of the liner.

The seam serves to seal the distal end area of the liner thereby enabling molding of the second polymeric layer over the first polymeric layer. As a result, the second polymeric layer is subsequently molded over the first polymeric layer after the seam is completely formed.

Embodiments of the invention are not limited to a seam located at a distal end area of the liner. Instead, multiple fabric sections may be combined to form the fabric layer. These fabric sections are preferably joined in a similar manner to the aforementioned seam, either by welding or stitching.

Figure 8:
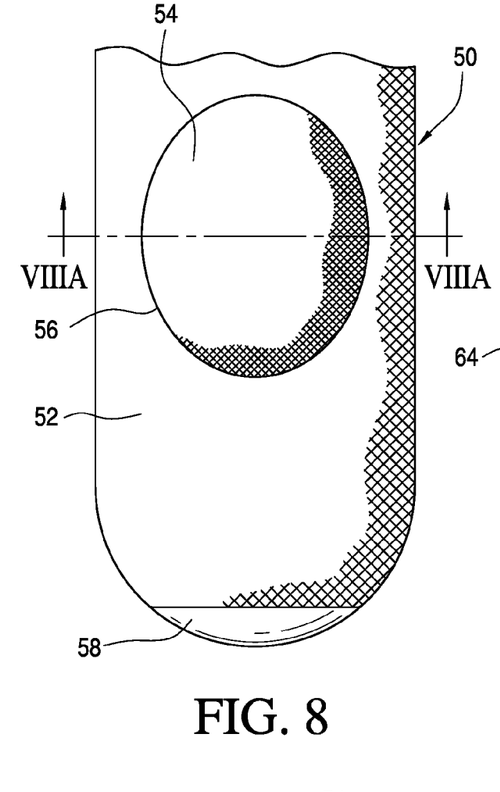
FIG. 8 is an elevational view showing an embodiment of the liner having first and second fabric sections forming a fabric layer.
Figure 8A:
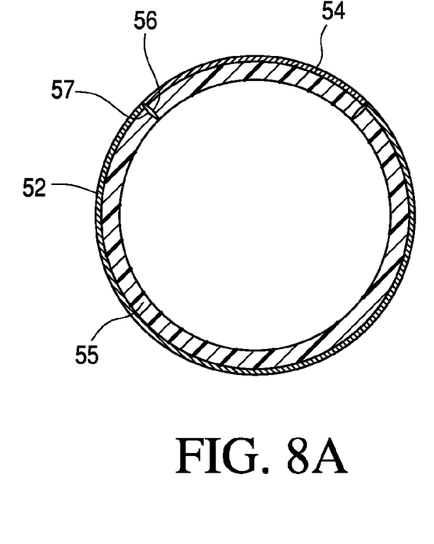
FIG. 8A is a cross-sectional view taken along line 8A-8A in FIG. 8.

In referring to FIGS. 8 and 8A, a liner 50 includes a second fabric section 54 secured to a first fabric section 52. The second fabric section 54 is surrounded in its entirety by the first fabric section 52, and joined along the seal 56. The seal 56 is arranged as described above in reference to other embodiments presented herein, and includes a welding element 57. The inner surface of the liner 50 is delimited by a layer of polymeric material 55 consistent with the other embodiments described herein.

As an alternative to any of the embodiments described herein, the liner 50 exemplifies a distal end cap 58 which may be secured to the distal end of the liner. The distal end cap may be mounted on the liner consistent with the practice discussed in U.S. Pat. No. 7,001,563.

The second fabric section 54 may have greater stiffness properties to accommodate certain anatomy of the residual limb, such as a knee. The second fabric section 54 may be arranged in a variety of different shapes according to the different anatomy it is to correspond to, and it may likewise be oriented according to desired results from the multiple section fabric layer. Moreover, the fabric layer may include a plurality of different fabric sections, preferably each connected to one another according to the aforementioned seams.

Figure 9:
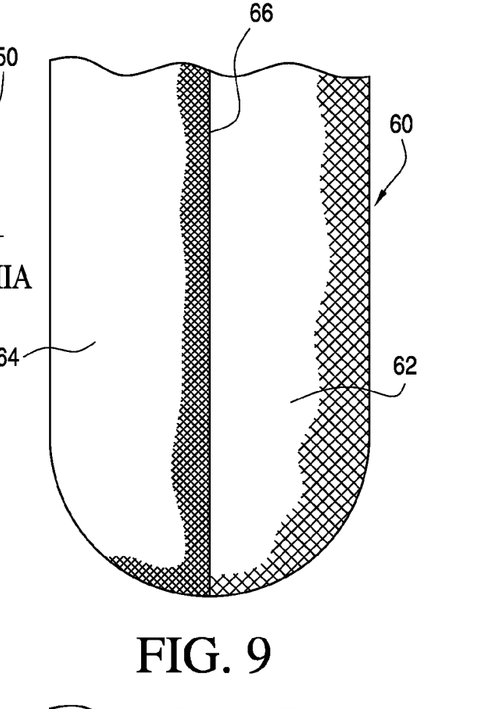
FIG. 9 is an elevational view showing another embodiment of the liner having first and second fabric sections forming a fabric layer.

FIG. 9 depicts another exemplary liner 60 wherein first and second fabric sections 62, 64 are secured to each other along a longitudinal seam 66. The first fabric section 62 may correspond to the anterior portion of the residual limb and the second fabric section 64 may correspond to the posterior portion of the residual limb.

Figure 10:
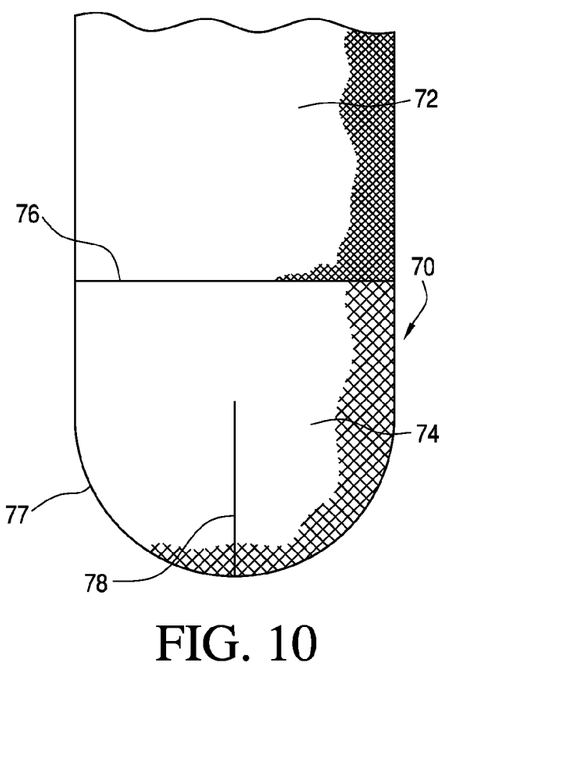
FIG. 10 is an elevational view showing yet another embodiment of the liner having first and second fabric sections forming a fabric layer.

In yet another exemplary embodiment, FIG. 10 illustrates a liner 70 having first and second circumferential fabric sections 72, 74 secured together along a circumferential seam 76. The first fabric section 72 may correspond to the distal end area of the liner so as to envelop the distal end area of the residual limb. The second fabric section 74 is arranged to at least envelop portions of the residual limb above or directed more towards a proximal end of the liner.

In each of these embodiments, the first and second fabric sections 72, 74 may have different properties, for example stiffness, surface texture, thickness, hardness.

Figure 11:
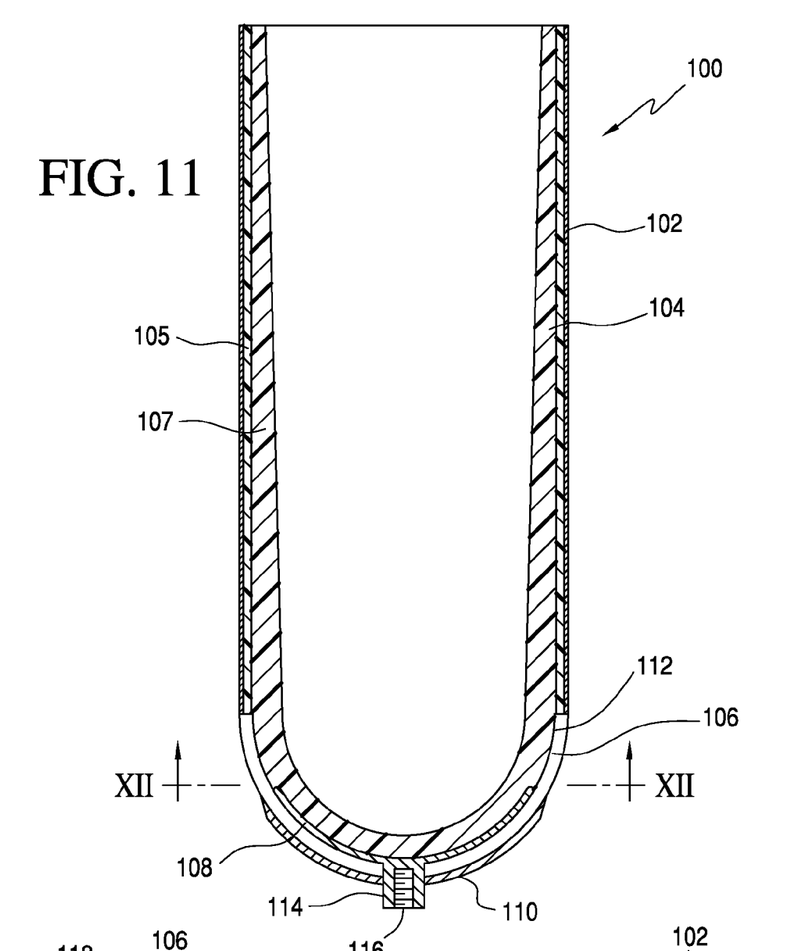
FIG. 11 is an elevational view showing an embodiment of a liner having an umbrella connector.
Figure 13:
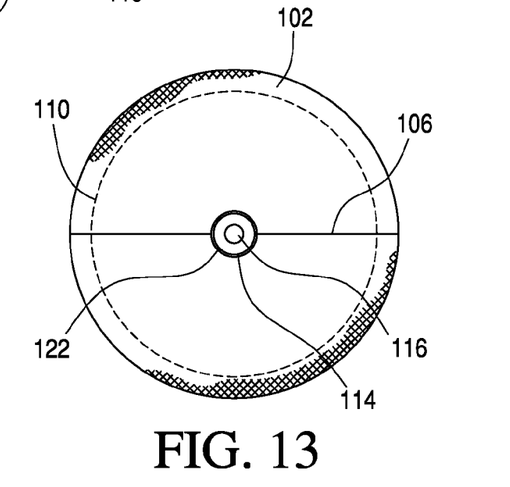
FIG. 13 is a bottom plan view of the liner of FIG. 11.

FIGS. 11 and 13 illustrate another embodiment of the liner 100 bearing similarity to the liner according to FIG. 1. This liner 100 includes a tubular fabric layer 102, and a polymeric layer 104 defined by first and second polymeric layers 105, 107. The liner defines a seam 106 having opposed edge portions 112, and arranged similarly to the seam described in FIG. 1. The seam 106 effectively closes the end of the shaped fabric layer 102, as in other embodiments described herein.

The liner of FIG. 11 includes an umbrella connector 108 embedded into the silicone layer 104. The umbrella connector 108 has a connecting end 114 having a threaded feature 116. As shown in FIG. 13, the connecting end 114 extends through an opening 122 formed through the fabric layer 102 and across the seam 106. The connecting end 114 is arranged to secure to various prosthetic devices and connectors known in the art of prosthetic devices. Because of the opening, a section of the fabric layer carrying the seam is removed while the seam remains intact. A distal end cap 110 is formed or bonded to the distal end area of the liner 100, and surrounds a portion of the connecting end 114. The shape of the umbrella connector is not limited to the variation shown herein and may also correspond to the umbrella connector in combination with a distal end cap as taught in U.S. Pat. No. 6,485,776.

Figure 12:
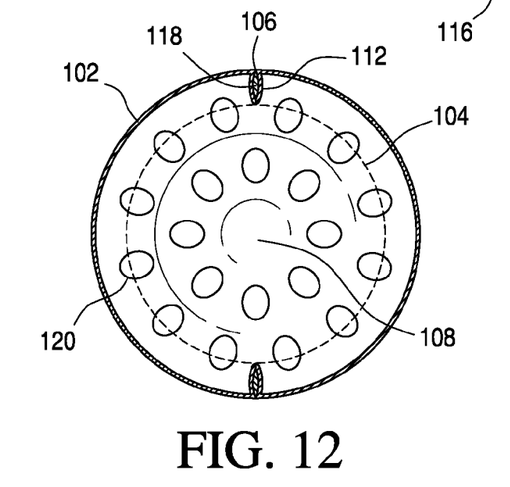
FIG. 12 is a cross-sectional view of the liner of FIG. 11 taken along line XII-XII without the silicone layer.

Referring to FIG. 12, the umbrella connector 108 is placed along the inner surface of the fabric layer 102 along its distal end. The umbrella connector 108 has a plurality of apertures 120 which facilitate embedding the umbrella connector 108 into the silicone layer 104. As with the other embodiments, the seam 106 includes the opposed edge portions 112 which are sealed by the welding element 118. The umbrella connector may be embedded into the liner and the distal end cap may be formed as taught in U.S. Pat. No. 6,485,776.

Figures 14, 15:
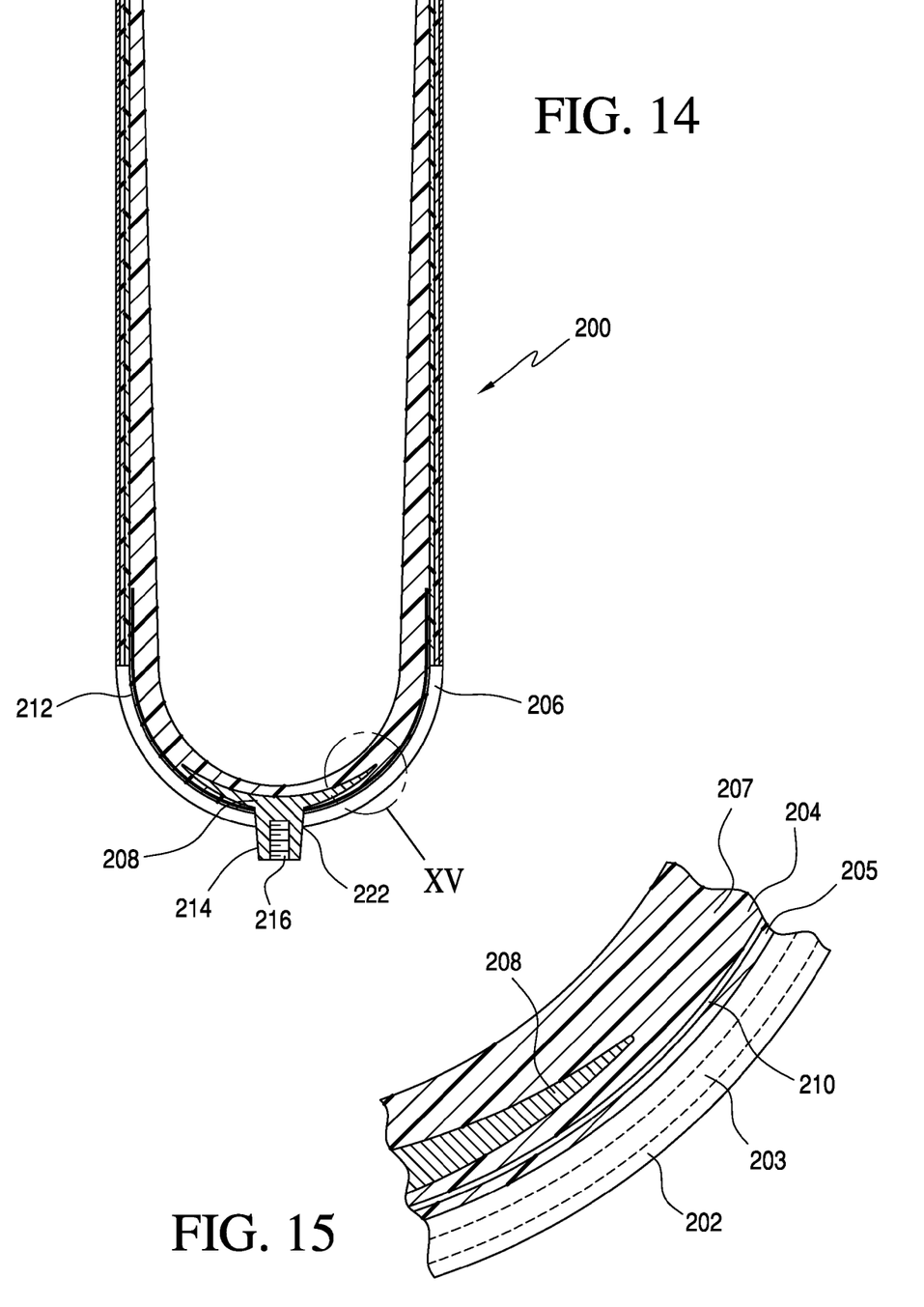
FIG. 14 is an elevational view showing another embodiment of a liner having an umbrella connector.
FIG. 15 is a sectional view taken from FIG. 14.

As illustrated in FIG. 14, another embodiment of a liner 200 includes an umbrella connector 208 in combination with a reinforcement matrix 210. The liner 200 includes a fabric layer 202, and first and second polymeric layers 203, 204. The reinforcement matrix 210 is located between the first second polymeric layers 203, 204. The second polymeric layer includes first and second layer portions 205, 207 on opposed sides of the umbrella connector 208. As depicted, the second layer portion 207 forms the majority of the thickness of the second polymeric layer 206.

The umbrella connector 210 in FIGS. 14 and 15 is arranged in a similar manner as in the liner 100 according to FIG. 11. Specifically, the liner 200 includes a seam 206 with opposed edge portions 212 embedded in at least one of the first and second polymeric layers 203, 204. The umbrella connector 210 includes a connecting end 214 which protrudes through an opening 222 formed through the fabric layer 202 and across the seam 206. The connecting end 214 includes a threaded feature 222 for securing to prosthetic devices.

By using a fabric layer closed at the distal end by a seam and then subsequently, forming a hole through the fabric layer for placement of a connecting end of an umbrella connector, manufacturing steps are eliminated resulting in reduced costs for making the process. A comparison can be made to the simplicity of the instant solution to the process described in U.S. Pat. No. 6,485,776.

Any of the liner embodiments described herein may be adapted to accommodate a plurality of undulations formed along portions of the liner in accordance with the description of U.S. Pat. Nos. 7,169,189 and 7,118,602, incorporated herein in their entirety by reference. Also, the liner embodiments may be configured to include a seal or seals described in U.S. Pat. No. 7,025,793, and U.S. patent application publication 2007/0123998, incorporated herein in their entirety by reference.

It will be understood that the aforementioned embodiments are not limited to the described liner described herein. Instead, the features of one of the preferred embodiments of this disclosure may readily be combined with those of another or other embodiments of the present disclosure without departing from the scope of the present invention.

It will be readily understood that the described embodiments of the disclosure are exemplary only and various other features and details could be incorporated in the liner described herein without departing from the spirit and scope of the invention as defined in the appended claims. Further, while the liner has been described in connection to a prosthetic liner, the embodiments may be adapted for any suitable prosthetic or orthopedic uses.

The invention claimed is:

1. A tubular prosthetic liner having an open proximal end and a closed-end distal area, and interior and exterior surfaces, the liner forming a cavity delimited by the interior surface, the liner adapted to envelop a residual limb, the liner comprising:
   a fabric layer defining first and second surfaces, the first fabric layer surface continuously defining the exterior surface of the liner; and
   a seam formed by opposed sides of the fabric layer joined together, the opposed sides of the fabric layer forming an excess portion directed toward the cavity of the liner;
   a first polymeric layer having first and second surfaces, the first surface of the first polymeric layer bonded to the second surface of the fabric layer, the excess portion embedded entirely in a thickness of the at least one polymeric layer;
   wherein the opposed sides of the fabric layer are joined together by a welding element along the opposed sides of the fabric layer.

2. The liner according to claim 1, wherein the seam is air-tight.

3. The liner according to claim 1, wherein the seam is formed across the distal end area of the liner and closing the distal end area of the fabric layer.

4. The liner according to claim 3, wherein the distal end area of the exterior and interior surfaces is continuous without interruption.

5. The liner according to claim 1, wherein the fabric layer is an elasticized fabric layer, the distal end area of the fabric layer arranged in a permanent distended condition.

6. The liner according to claim 1, wherein the at least one polymeric layer includes:
   a second continuous polymeric layer having first and second surfaces, the first second layer surface being contiguous and integrally secured to the second first layer surface, the second polymeric layer being thicker than the first polymeric layer, the second layer surface forming the interior surface as a continuously smooth surface.

7. The liner according to claim 6, wherein the second polymeric layer has a hardness substantially less than a hardness of the first polymeric layer.

8. The liner according to claim 6, wherein the first polymeric layer has a thickness substantially less than a thickness pertaining to the second polymeric layer.

9. The liner according to claim 6, wherein the second polymeric layer is formed from a material selected from the group consisting a silicone elastomer, a composite including a silicone elastomer and silicone oil dispersed through the silicone elastomer, or a composite including a silicone elastomer containing a plurality of hollow microspheres dispersed through the silicone elastomer.

10. The liner according to claim 6, further comprising a distension controlling reinforcement matrix embedded in the second polymeric layer over the distal end area of the liner, the reinforcement matrix contains reinforcement elements providing stiffness against elongation of the liner in a direction along a liner length without providing resistance against distension of the second polymeric layer in directions transverse to the liner length.

11. The liner according to claim 1, wherein the fabric layer is formed of first and second fabric sections joined together along the seam.

12. The liner according to claim 1, wherein the liner distal end area has an arcuate outer wall defining radii of curvature centered along a liner longitudinal axis of external symmetry, the seam tracing at least along the radii of curvature.

13. A tubular prosthetic liner having an open proximal end and a closed-end distal area, and interior and exterior surfaces having a cavity defined by the interior surface, the liner adapted to envelop a residual limb, the liner comprising:
   first and second fabric sections each defining first and second surfaces joined together along a seam;
   a first polymeric layer having first and second surfaces, the first surface of the first polymeric layer bonded to interior surfaces of the first and second fabric sections;
   the seam is formed by opposed sides of the first and second fabric sections joined together, the opposed sides of the first and second fabric sections forming an excess portion directed toward the cavity of the liner;
   wherein the excess portion of the seam is embedded entirely in a thickness of the at least one polymeric layer, the interior surface of the liner having a continuously smooth surface without interruption;
   wherein the opposed sides of the first and second fabric sections are joined together by a welding element, the welding element is a polymeric film contiguously and integrally joined along the opposed sides of the first and second fabric sections.

14. The liner according to claim 13, wherein the seam is an air-tight seam.

15. A tubular prosthetic liner having an open proximal end and a closed-end distal area, and interior and exterior surfaces having a cavity defined by the interior surface, the liner adapted to envelop a residual limb, the liner comprising:
   first and second fabric sections each defining first and second surfaces joined together along a seam;

a first polymeric layer having first and second surfaces, the first surface of the first polymeric layer bonded to interior surfaces of the first and second fabric sections;

the seam is formed by opposed sides of the first and second fabric sections joined together, the opposed sides of the first and second fabric sections forming an excess portion directed toward the cavity of the liner;

wherein the excess portion of the seam is embedded entirely in a thickness of the at least one polymeric layer, the interior surface of the liner having a continuously smooth surface without interruption;

wherein the two fabric sections have different stiffness properties.

\* \* \* \* \*